United States Patent [19]  [11] 4,179,570
Oude Alink  [45] Dec. 18, 1979

[54] PYRIDINES AND DIHYDROPYRIDINES

[75] Inventor: Bernardus A. Oude Alink, St. Louis, Mo.

[73] Assignee: Petrolite Corporation, St. Louis, Mo.

[21] Appl. No.: 970,415

[22] Filed: Dec. 18, 1978

[51] Int. Cl.$^2$ .................. C07D 213/16; C07D 211/70
[52] U.S. Cl. .................................................... 546/252
[58] Field of Search ........................................ 346/252

[56] References Cited
U.S. PATENT DOCUMENTS 3,931,191  1/1976  Oude Alink ........................ 546/252
4,022,785  5/1977  Oude Alink et al. ................ 562/252

Primary Examiner—Alan L. Rotman
Assistant Examiner—Robert T. Bond
Attorney, Agent, or Firm—Sidney B. Ring; Hyman F. Glass

[57] ABSTRACT

A process of preparing alkyl (or aralkyl) pyridines and N-substituted alkyl (or aralkyl) dihydropyridines which comprises treating a 2,5,6,8,9-pentaalkyl (or aralkyl) substituted 1,3,7-triazabicyclo (3,3,1) non-3-ene with a Lewis acid.

6 Claims, No Drawings

PYRIDINES AND DIHYDROPYRIDINES

In patent application Ser. No. 932,088 filed Aug. 8, 1978, the following is described and claimed:

(1) The reaction of an aldehyde with ammonia to yield 2,4,6-trialkyl-1,3,5-hexahydrotriazines (Formula I) in accord with the equation

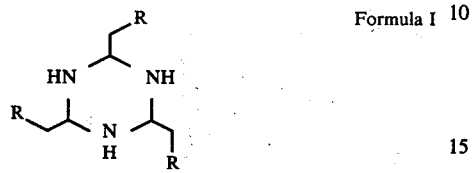

Formula I (2) The deammoniation of Formula I to yield N,N'-dialkylidene 1,1-diaminoalkane (Formula II) in accord with the equation

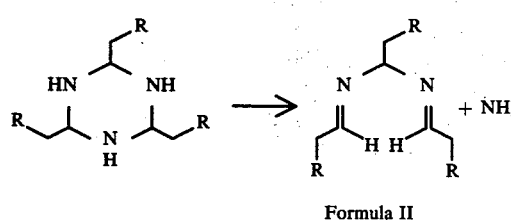

Formula II (3) The reaction of N,N'-dialkylidene 1,1-diaminoalkanes in the presence of a Lewis acid to form 2,5,6,8,9-penta-alkyl (or aralkyl)-substituted 1,3,7-triazabicyclo (3,3,1) non-3-enes's (TBN's), or mixtures thereof, according to the equation:

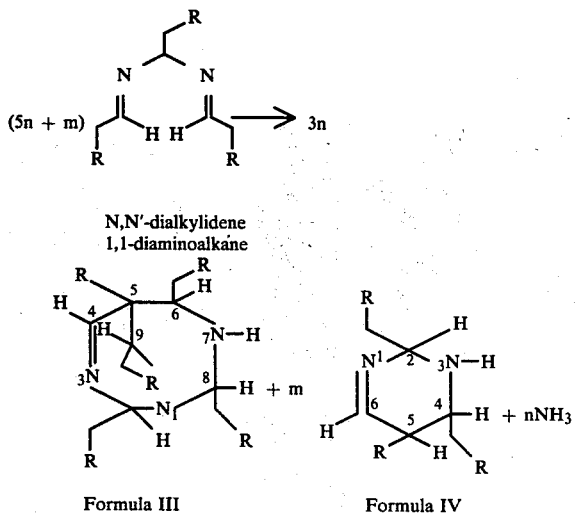

N,N'-dialkylidene 1,1-diaminoalkane

Formula III — 2,5,6,8,9-Penta alkyl (or aralkyl) substituted 1,3,7-triazabicyclo (3,3,1)non-3-ene (TBN)

Formula IV — 2,4,5-Trialkyl (or aralkyl) substituted tetrahydropyrimidine (THP)

In U.S. Pat. No. 4,022,785 issued May 10, 1977 there is described and claimed a process of preparing alkyl-pyridines and N-substituted alkyl dihydropyrimidines by reacting a hexahydrotriazine in the presence of a Lewis acid.

I have now discovered that 2,5,6,8,9-penta-alkyl (or aralkyl) substituted 1,3,7-triazabicyclo(3,3,1) non-3-enes (TBN's) can be reacted in the presence of a Lewis acid to form mixtures of alkyl (or aralkyl) pyridines and N-substituted alkyl (or aralkyl) dihydropyridines according to the equation:

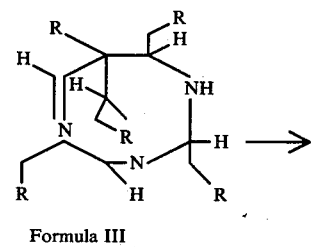

Formula III 2,5,6,8,9-Penta alkyl (or aralkyl) substituted 1,3,7-triazabicyclo (3,3,1)non-3-ene (TBN)

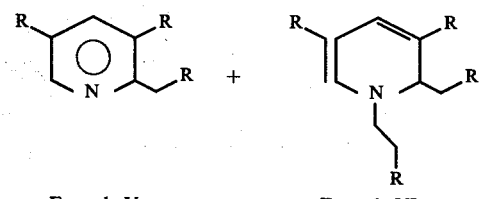

Formula V — 2,3,5-Trialkyl (or aralkyl) substituted pyridine

Formula VI — 1,2,3,5-tetra alkyl (or aralkyl) substituted 1,2-dihydropyridine

The reaction can also be carried out by heating the mixture 2,5,6,8,9-Penta-alkyl (or aralkyl) substituted 1,3,7-triazabicyclo (3,3,1) non-3-ene and 2,4,5-trialkyl (or aralkyl) substituted tetrahydropyrimidine in the presence of a Lewis acid until conversion to the pyridine and dihydropyridine is effected.

Although reaction conditions such as time, temperature, solvent (if employed), etc., can vary widely, the preferred conditions will depend on various factors such as the particular reactants, the particular Lewis acid, the interrelationship of conditions, etc. Thus, any suitable reaction time, temperature, solvent, Lewis acid, etc., can be employed provided the desired products are produced.

Reaction conditions required to convert the TBN to pyridines and dihydropyridines may be summarized as follows:

Temperature

From about 100°–300° C., such as from about 110°–250° C., but preferably from about 120°–220° C.

Time

From about 0.5–48 hours such as from about 1–24 hours, but preferably from about 1–18 hours.

Solvent

The reaction can be carried out with or without a solvent. If a solvent is used, any solvent can be used as long as it does not interfere with the reactants, for example, aliphatic hydrocarbons such as heptanes, octanes, etc.; aromatic solvents such as benzene, toluene, xylenes, etc.; alcohols such as pentanol, hexanol, decanol, etc.

Catalyst

Any suitable Lewis acid can be employed such as $AlCl_3$, $ZnCl_2$, $FeCl_3$, $BF_3$, $SnCl_4$, $NH_4I$, $NH_4Br$, $NH_4Cl$, $NH_4$ acetate, etc. A weak Lewis acid is preferred such as ammonium chloride, ammonium acetate, etc.

R Group

Any suitable aldehyde can be employed such as alkyl, etc., but preferably linear alkyl aldehydes. The reaction can also be effected with other aldehydes, preferably where a second methylene to the aldehyde group is present, i.e., $$R'-CH_2-CH_2-\overset{O}{\underset{\|}{C}}-H$$

including aralkyl, etc. groups.

Thus, alkyl groups having from about 1 to 30 carbons such as from about 1–18 carbons, for example from about 1–12 carbons, but preferably lower alkyls having from about 1–8 carbons, can be employed.

Yields

They are substantially quantitative for conversion of TBN to pyridines and dihydropyridines.

The 2,5,6,8,9-Penta-alkyl (or aralkyl)-substituted 1,3,7-triazabicyclo (3,3,1) non-3-ene used in preparing pyridines and dihydropyridines may exist as any of 16 possible stereo-isomers. The following two stereo-isomers were used:

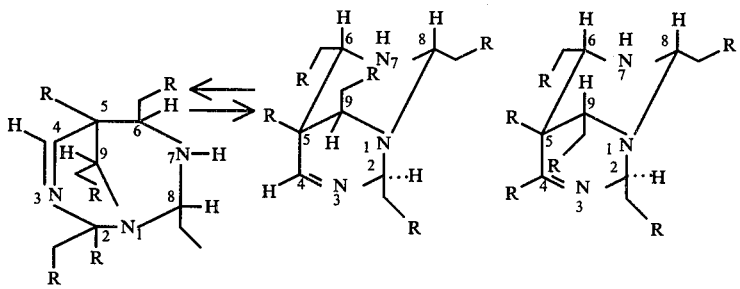

The difference between the two isomers is in the attachment of the 9—CH₂—R group.

The following examples are presented by way of illustration and not of limitation.

EXAMPLE 1

5-Methyl-2,6,8,9-tetraethyl-1,3,7-triazabicyclo (3,3,1) non-3-ene

A sample of 1330 cc of 28% ammonium hydroxide was cooled to 2° C. Over a 2 hours period 290 grams of propionaldehyde was added, while a reaction temperature of 0°–10° C. was maintained. The resulting solution was kept for 4 days at about 5° C., after which time 400 grams of sodium chloride was added. The product was extracted three times with ether, and the ethereal solution after drying over anh. MgSO₄ evaporated under diminished pressure to yield 119 grams of 2,4,6-triethyl 1,3,5-hexahydrotriazine. ¹³C nuclear magnetic resonance spectrum, solvent CDCl₃, internal reference tetramethylsilane, δ in ppm:

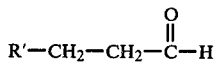

71.8 (1); 29.8 (2); 9.4 (3).

A mixture of 117 grams of 2,4,6-triethyl 1,3,5-hexahydrotriazine, 117 grams of hexanes (b.p. 65.8°–67.8° C.) and 1.5 grams of ammonium chloride was refluxed under azeotropical conditions for 5 hours. Ammonia gas was evolved during the reaction. The reaction mixture after cooling to ambient temperature was concentrated under diminished pressure to yield 97 grams of product. A sample of 16 grams of the product was distilled under diminished pressure from 3 pellets of sodium hydroxide, and the fraction 11.5 grams of b.p. 83°–86° C./0.06 torr was identified as a mixture of two stereoisomers of 5-methyl-2,6,8,9-tetraethyl 1,3,7-triazabicyclo (3,3,1) non-3-ene. Anal. Calculated for C₁₅H₂₉N₃: N, 16.73%; Found: N, 16.69%. Upon standing, the isomer with the 9-ethyl group in the axial position with respect to the hexahydropyrimidine ring crystallized from the mixture, m.p. 74°–76° C.; Infrared spectrum, KBr pellet, 3.08μ (N—H) and 6.08μ (C=N); ¹H nuclear magnetic resonance spectrum, solvent CDCl₃, internal reference tetramethylsilane. δ in ppm: 7.58, d, 1H; 4.45, m, 1H; 3.67, t, 1H; 2.90–2.40 m's, 2H; 1.92–1.13 m's, 8H; 1.13–0.60 m's, 15H. ¹³C. nuclear magnetic resonance spectrum, solvent CDCl₃, internal reference tetramethylsilane, δ in ppm:

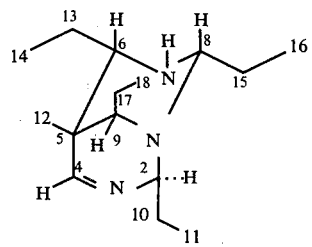

68.7 (2); 167.8 (4); 37.4 (5); 60.5 (6); 74.2 (8); 57.8 (9); 23.6 (10); 10.9 (11); 19.9 (12); 27.9 (13); 11.6 (14); 26.5 (16); 16.8 (17); 12.1 (18).

Anal. Calculated for C₁₅H₂₉N₃; C, 71.71; H, 11.55; N, 16.73.

Found: C, 71.62; H, 11.63; N, 16.58.

The other isomer was identified as having a 9-ethyl group in the equatorial position, with respect to the hexahydropyrimidine ring. $^{13}$C nuclear, magnetic resonance spectrum, solvent CDCl$_3$, internal reference tetramethylsilane, δ in ppm:

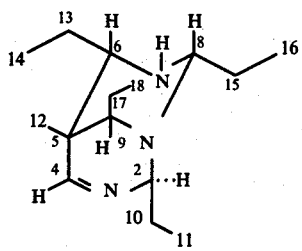

73.0 (2); 165.3 (4); 38.5 (5); 67.1 (6); 80.7 (8); 68.4 (9); 30.4 (10); 11.4 (11); 18.2 (12); 27.8 (13); 11.7 (14); 24.0 (15); 10.5 (16); 22.6 (17); 12.6 (18).

EXAMPLE 2

5-Ethyl-2,6,8,9-tetrapropyl 1,3,7-triazabicyclo (3,3,1) non-3-ene

To a sample of 606 grams of 28% ammonium hydroxide was added over a 1 hour period 321 grams of butyraldehyde at a reaction temperature of 25°–29° C. After the addition was completed, the mixture was stirred for 2 more hours at ambient temperature. The organic layer was separated and dissolved in hexanes. The hexane solution after drying over anh. MgSO$_4$, was evaporated under diminished pressure to yield 278.8 grams of 2,4,6-tripropyl 1,3,5-hexahydrotriazine, $^{13}$C nuclear magnetic resonance spectrum, solvent CDCl$_3$, internal reference tetramethylsilane, δ in ppm:

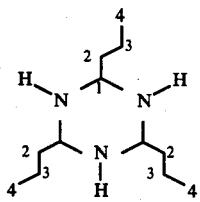

70.3 (1); 39.5 (2); 18.4 (3); 14.2 (14)

A mixture of 146.4 grams of 2,4,6-tripropyl 1,3,5-hexahydrotriazine and 267 grams of hexanes was refluxed under azeotropical conditions for 19 hours. The hexanes were removed under diminished pressure to yield 121.6 grams of N,N'-dibutylidene-1,1-diaminobutane, $^{13}$C nuclear magnetic resonance spectrum, solvent CDCl$_3$, internal reference tetramethylsilane, δ in ppm:

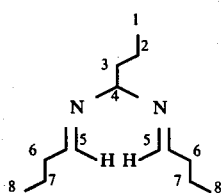

13.8 (1); 18.6 (2); 40.0 (3); 91.3 (4); 163.5 (5); 38.0 (6); 19.5 (7); 14.1 (8).

A mixture of 120 grams of N,N'-dibutylidene 1,1-diaminobutane, 1.3 grams of acetic acid and 158 grams of hexanes (b.p. 65.8°–67.8° C.) was refluxed for 1 hour. The hexanes were removed under diminished pressure to yield 118 grams of a mixture of 20% 2,4-dipropyl 5-ethyl 2,3,4,5-tetrahydropyrimidine, $^{13}$C nuclear magnetic resonance spectrum, solvent CDCl$_3$, internal reference tetramethylsilane,

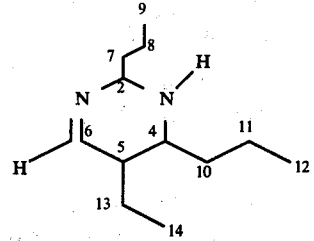

72.9 (2); 53.5 (4); 44.6 (5); 164.1 (6); 39.8 (7); 18.8 (8); 14.2 (9); 36.7 (10); 19.2 (11); 14.2 (12); 22.5 (13); 10.5 (14). 15% of 5-ethyl 2,6,8,9-tetrapropyl 1,3,7-triazabicyclo (3,3,1) non-3-ene, with the 9 ethyl group in the equatorial position, with respect to the hexahydropyrimidine ring and 65% of 5-ethyl 2,6,8,9-tetrapropyl 1,3,7-triazabicyclo (3,3,1) non-3-ene with the 9 ethyl group in the axial position with respect to the hexahydropyrimidine ring; Infrared spectrum, 3.05μ (N—H) and 6.05μ (C=N), $^1$H nuclear magnetic resonance spectrum, solvent CDCl$_3$, internal reference tetramethylsilane, δ in ppm: 7.57, 1H; 4.54, 1H; 3.78, 1H; 2.98 and 2.84, 2H; 1.1-2.2, 18H; and 0.95, 15H. $^{13}$C nuclear magnetic resonance spectrum, solvent CDCl$_3$, internal reference tetramethylsilane, δ in ppm:

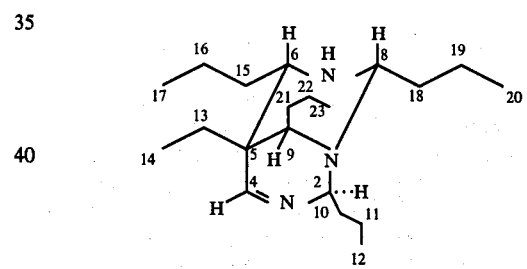

66.9 (2); 167.6 (4); 40.2 (5); 50.3 (6); 72.5 (8); 58.0 (9); 32.5 (10); 19.6 (11); 14.2 (12); 25.0 (13); 8.1 (14); 37.4 (15); 20.0 (16); 14.2 (17); 36.0 (18); 18.5 (19); 14.2 (20); 25.5 (21); 20.3 (22); 14.2 (23).

EXAMPLE 3

5-Propyl 2,6,8,9-tetrabutyl 1,3,7-triazabicyclo (3,3,1) non-3-ene

To a sample of 560 cc of 28% ammonium hydroxide was added with stirring 179 grams of valeraldehyde over 1½ hours while a reaction temperature of 20°–42° C. was maintained. Stirring was continued for 2 hours at ambient temperature. The organic layer which separated was taken up in hexanes and the hexane solution after drying over sodium hydroxide was evaporated under diminished pressure to yield 169.5 grams of 2,4,6-tributyl 1,3,5-hexahydrotriazine. $^{13}$C nuclear magnetic resonance spectrum, solvent CDCl$_3$, internal reference tetramethylsilane, δ in ppm:

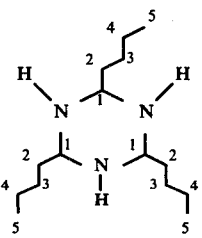

70.5 (1); 37.0 (2); 27.3 (3); 22.7 (4); 13.9 (5).

A mixture of 168.8 grams of 2,4,6-tributyl 1,3,5-hexahydrotriazine, 228 grams of hexanes, and 1.5 grams of ammonium chloride were refluxed for 2 hours. A sample of 3 grams of solution was removed to determine the $^{13}$C nuclear magnetic resonance spectral characteristics of the product. After 2 hours reaction the product was identified as mainly N,N'-dipentylidene 1,1-diaminopentane. $^{13}$C nuclear magnetic resonance spectrum, solvent CDCl$_3$, internal reference tetramethylsilane, δ in ppm:

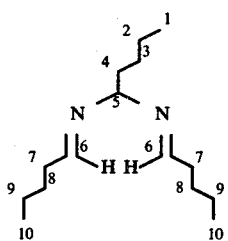

14.2 (1); 22.5 (2); 27.7 (3); 37.4 (4); 91.4 (5); 163.5 (6); 35.7 (7); 28.3 (8); 22.9 (9); 14.2 (10).

Reflux of the remaining hexane solution was continued for 17 hours. The solution was filtered and the solvent removed under diminished pressure to yield 157 grams of a mixture of 20% 2,4-dibutyl 5-propyl 2,3,4,5-tetrahydropyrimidine, 10% of 5-propyl-2,6,8,9-tetrabutyl 1,3,7-triazabicyclo (3,3,1)non-3-ene, the isomer with the 9 butyl group in the equatorial position with respect to the hexahydropyrimidine, and 70% of 5-propyl 2,6,8,9-tetrabutyl 1,3,7-triazabicyclo (3,3,1) non-3-ene, the isomer with the 9 butyl group in the axial position. Infrared spectrum, 3.04μ (N–H) and 6.04μ (C=N). $^{13}$C nuclear magnetic resonance spectrum, solvent CDCl$_3$, internal reference tetramethylsilane, δ in ppm:
67.0 (2); 167.5 (4); 40.3 (5); 51.2 (6); 72.6 (8); 58.2 (9); 30.0 (10); 28.6 (11); 22.7 (12); 14.0 (13); 34.8 (14) 17.0 (15); 14.9 (16); 35.1 (17) 29.1 (18); 22.7 (19); 14.0 (20) 33.5 (21); 27.5 (22); 22.7 (23) 14.0 (24); 22.3 (25); 29.6 (26) 22.7 (27); 14.0 (28).

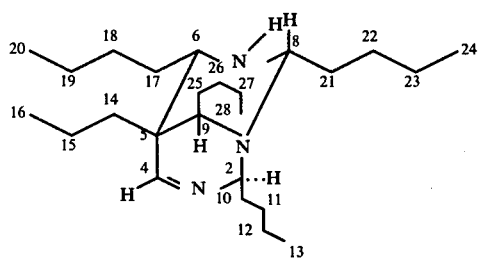

EXAMPLE 4

1-Butyl-2-propyl-3,5-diethyl-1,2-dihydropyridine and 2-propyl-3,5-diethylpyridine.

A mixture of 160.5 grams of 5-ethyl-2,6,8,9-tetrapropyl-1,3,7-triazabicyclo (3,3,1) non-3-ene and 1 gram of acetic acid was heated over a 1 hour period to 185° C. and kept at this temperature for 5 hours. During this time ammonia gas was evolved. The resulting 148 grams of product was identified as a mixture of 1 part 1-butyl- 2-propyl-3,5-diethyl-1,2-dihydropyridine; $^1$H nmr δ ppm, solvent CDCl$_3$, 5.61 m (2H, C=C$\underline{H}$), 3.59 m (1H, NC$\underline{H}$), 2.87 t (2H, NC$\underline{H}_2$), 2.05 m (4H, C=C—C$\underline{H}_2$CH$_3$), 1.33 m and 1.01 m (20H, C$\underline{H}_2$—C$\underline{H}_2$ and C$\underline{H}_3$); $^{13}$C nmr δ ppm, solvent CDCl$_3$, 128.2, 128.0, 119.7, 111.4, 60.2, 54.2, 34.3, 32.4, 27.7, 25.6, 20.1, 18.8, 14.9, 14.6, 14.0 and 12.6. Anal. Calcd. for C$_{10}$H$_{29}$N: N, 5.96. Found: N, 5.81. And 2 parts of 2-propyl-3,5-diethylpyridine; $^{13}$C nmr δ in ppm, solvent CDCl$_3$, 157.2, 146.1, 136.5, 135.4, 146.1, 36.5, 25.8, 25.2, 22.9, 15.3, 14.9 and 14.2 Calcd. for C$_{12}$H$_{19}$N: 7.91. Found: N, 7.85

According to the method described in example 4, several pentaalkyl-1,3,7-triazabicyclo (3,3,1) non-3-enes derived from aldehydes and mixed aldehydes were reacted. The results are summarized in Table I.

Table I

| Example Number | Pentaalkyl-1,3,7-triaza-bicyclo (3,3,1) non-3-enes derived from aldehyde(s) | Product |
| --- | --- | --- |
| 5 | Propionaldehyde (as described in ex. 1) | 1-propyl-2-ethyl-3,5-dimethyl-1,2-dihydropyridine and 2-ethyl-3,5-dimethyl pyridine |
| 6 | Valeraldehyde (as described in ex. 3) | 1-pentyl-2-butyl-3,5-dipropyl-1,2-dihydropyridine and 2-butyl-3,5-dipropylpyridine |
| 7 | Propionaldehyde and Butyraldehyde | mixture of N-substituted alkyl dihydropyridines and alkylpyridines |

The products of this invention are useful as corrosion inhibitors, biocides, fuel additives, etc. For example, the products of examples 4–7 are useful as corrosion inhibitors.

I claim:

1. A process of preparing alkyl (or aralkyl) pyridines and N-substituted alkyl (or aralkyl) dihydropyridines which comprises treating a 2,5,6,8,9-pentaalkyl (or aralkyl) substituted 1,3,7-triazabicyclo (3,3,1) non-3-ene with a Lewis acid, in the presence or absence of a solvent and at a temperature range of from 100 to 300 degrees C.

2. The process of claim 1 where the products of the reaction are 2,3,5-trialkyl (or aralkyl) substituted pyridines and 1,2,3,5-tetraalkyl (or aralkyl) substituted 1,2-dihydropyridines.

3. The process of claim 2 where 5-ethyl-2,6,8,9-tetrapropyl-1,3,7-triazabicyclo (3,3,1) non-3-ene is converted to 1-butyl-2-propyl-3,5-diethyl-1,2-dihydropyridine and 2-propyl-3,5-diethylpyridine.

4. The process of claim 2 where 5-methyl-2,6,8,9-tetraethyl-1,3,7-triazabicyclo (3,3,1) non-3-ene is converted to 1-propyl-2-ethyl-3,5-dimethyl-1,2-dihydropyridine and 2-ethyl-3,5-dimethylpyridine.

5. The process of claim 2 where 5-propyl-2,6,8,9-tetrabutyl-1,3,7-triazabicyclo (3,3,1) non-3-ene is converted to 1-pentyl-2-butyl-3,5-dipropyl-1,2-dihydropyridine and 2-butyl-3,5-dipropylpyridine.

6. The process of claim 2 where a mixture of 2,5,6,8,9-pentaalkyl (or aralkyl) substituted 1,3,7-triazabicyclo (3,3,1) non-3-ene and 2,4,5-trialkyl (or aralkyl) 2,3,4,5-tetrahydropyrimidine are converted to alkyl (or aralkyl) pyridines and N-substituted alkyl (or aralkyl) dihydropyridines.

* * * * *